(12) United States Patent
Norlander et al.

(10) Patent No.: US 6,562,049 B1
(45) Date of Patent: May 13, 2003

(54) MEDICAL INTRODUCER APPARATUS

(75) Inventors: Barry E. Norlander, Pittsburgh, PA (US); William J. Boyle, Lower Burrell, PA (US)

(73) Assignee: Cook Vascular Incorporated, Leechburg, PA (US)

( * ) Notice: Subject to any disclaimer, the term of this patent is extended or adjusted under 35 U.S.C. 154(b) by 218 days.

(21) Appl. No.: 09/710,112

(22) Filed: Nov. 9, 2000

Related U.S. Application Data
(60) Provisional application No. 60/185,996, filed on Mar. 1, 2000.

(51) Int. Cl.[7] ................................................. A61F 11/00
(52) U.S. Cl. ..................................................... 606/108
(58) Field of Search ................................ 606/108, 192, 606/194, 213, 1, 215, 198, 191, 200; 604/160, 161, 96, 95, 283, 102, 164

(56) References Cited

U.S. PATENT DOCUMENTS

| | | | |
|---|---|---|---|
| 4,306,562 A | | 12/1981 | Osborne |
| 4,581,025 A | | 4/1986 | Timmermans |
| 5,066,285 A | | 11/1991 | Hillstead |
| 5,066,772 A | * | 11/1991 | Tang et al. .................. 528/354 |
| 5,106,368 A | | 4/1992 | Uldall et al. |
| 5,171,222 A | | 12/1992 | Euteneuer et al. |
| 5,221,255 A | | 6/1993 | Mahurkar et al. |
| 5,250,038 A | | 10/1993 | Melker et al. |
| 5,409,469 A | | 4/1995 | Schaerf |
| 5,415,639 A | * | 5/1995 | VandenEinde et al. ....... 604/283 |
| 5,454,790 A | | 10/1995 | Dubrul |
| 5,533,968 A | * | 7/1996 | Muni et al. .................... 604/96 |
| 5,562,620 A | | 10/1996 | Klein et al. |
| 5,618,267 A | | 4/1997 | Palestrant |
| 5,628,754 A | * | 5/1997 | Shevlin et al. ............... 606/108 |
| 5,645,533 A | * | 7/1997 | Blaeser et al. ............... 604/164 |
| 5,725,512 A | | 3/1998 | Swartz et al. |
| 5,725,551 A | * | 3/1998 | Myers et al. ................. 606/213 |

(List continued on next page.)

FOREIGN PATENT DOCUMENTS

| | | |
|---|---|---|
| EP | 0916360 | 5/1999 |
| WO | 9710870 | 3/1997 |
| WO | 9930762 | 6/1999 |

OTHER PUBLICATIONS

Curved Multipurpose Introducer Set; Catheter Introducers; Cook Incorporated Diagnostic and Interventional Products Catalog; 2000.

Primary Examiner—John J. Calvert
Assistant Examiner—Alissa L. Hoey
(74) Attorney, Agent, or Firm—Charles W. Agnew

(57) ABSTRACT

An introducer apparatus (10) comprising a pair of co-extending splittable introducer sheaths (11), (12) is disclosed. The unique properties (pushability, torqueability, length, shape, etc.) of the individual introducer sheaths yields an introducer apparatus with the additional navigational flexibility to reach a remote target that whose access would be more difficult or impossible with a single introducer sheath. One embodiment include a coaxial pair of introducer sheaths made of made of molecularly oriented (non-isotropic) polytetrafluoroethylene PTFE which are used for placement of a pacemaker or defibrillator lead into the coronary sinus. In this embodiment, the first introducer sheath (11) is introduced over a wire guide into ostium of the coronary sinus, which represents the first target site. The outer introducer sheath includes preformed bends (20) to facilitate passage through the vasculature. A second introducer sheath (12), which includes a curved distal portion (17), is introduced through the first introducer where it extends from the distal end of the outer introducer sheath to access the second, ultimate target site, such as a coronary artery branching from the coronary sinus. After the pacemaker lead has been placed, both sheaths are split and removed from the patient.

33 Claims, 5 Drawing Sheets

U.S. PATENT DOCUMENTS 5,976,107 A * 11/1999 Mertens et al. ................ 604/96
6,007,517 A * 12/1999 Anderson .................... 604/96
6,027,475 A * 2/2000 Sirhan et al. ................. 604/96
6,190,349 B1   2/2001 Ash et al.
6,264,671 B1 * 7/2001 Stack et al. ................. 606/198
6,394,978 B1 * 5/2002 Boyle et al. ........... 604/103.06
6,409,863 B1 * 6/2002 Williams et al. ............ 156/198
6,419,674 B1 * 7/2002 Bowser et al. ................ 606/45

* cited by examiner

MEDICAL INTRODUCER APPARATUS

CROSS-REFERENCE TO RELATED APPLICATIONS

This application claims priority of provisional application Ser. No. 60/185,996 filed Mar. 1, 2000.

TECHNICAL FIELD

The invention relates to medical devices, and more particularly to introducer sheaths and the like.

BACKGROUND OF THE INVENTION

Introducer sheaths are used as conduits for the placement of intravascular medical devices into venous or arterial systems following percutaneous access using the Seldinger technique. The introducer sheath is placed into a major blood vessel and the introduced device is then advanced from the distal end of the sheath and maneuvered to the target site by the physician, usually under fluoroscopy. In the case of placement of devices such as pacemaker and defibrillator leads which have large proximal connectors, splittable sheaths are used so that the sheath can be removed from the patient without disturbing the lead which must be left in place.

While current introducer sheaths for placing pacemaker leads and other intravascular devices are adequate for most applications, new pacing technologies and strategies, such as Intracoronary Cardioverter Defibrillation (ICD) and biventricular pacing, have been developed that require placing leads into the coronary sinus or into the coronary vessels themselves. Accessing these anatomical sites is difficult to impossible with current introducer devices whose function is generally limited to establishing a conduit through a relatively large vessel to site that is relative easy to access. One problem is that pacemaker leads and other such devices are not particularly designed to have good pushability and torqueability. This especially true for leads inserted into or via the coronary sinus since they are generally thinner and even more flexible than their standard counterparts. While the reduced pushability and torqueability does not normally pose a concern regarding placement of right atrial and ventricular leads, it can be a problem when placing a lead to stimulate the left side of the heart. For example, one method is to access the peripheral or central vessel using a standard splittable sheath, as is currently done, then trying to push and maneuver the lead further, to enter the ostium of the coronary sinus. This approach has proven to be very time-consuming and quite difficult to accomplish, especially if the cardiac vessels are to be accessed. In the case of standard straight splittable sheaths made of polytetrafluoroethylene (PTFE) such as a PEEL-AWAY™ Introducer Sheath (Cook Incorporated, Bloomington, Ind.), merely lengthening the sheath creates difficulties in that long PTFE sheaths are prone to kinking when being negotiated through a tortuous path, while the pre-scored sheaths made from other materials lack the pushability and torqueability to be guided through such a long, tortuous path. While adding a curve to the PTFE introducer will help in negotiating an initial tortuous bend, such as found in the subclavian and innominate veins, when a second, distal tortuous turn is required to access the target site, such as in the right atrium, the introducer sheath is not designed to make that bend. Additionally, to access a smaller target vessel such as the coronary sinus, a small introducer sheath is required that would lack the pushability and torqueability to be successfully maneuvered to that site without being prone to kinking. A second method has been to use a preformed guiding catheter to access the coronary sinus and associated vessels, then introducing the lead into the guiding catheter for placement. The primary disadvantage with this approach is that it is very difficult to remove the guiding catheter, which is not splittable, over the lead without dislodging it from the target site due to the amount of friction between the devices.

What is needed is an introducer system that can provide quicker and easier placement of a pacing lead or other device through a complex tortuous path to a remote anatomical location, especially where the target location requires a small-diameter introducer. Desirable properties of such a system would include splittability, resistance to kinking, minimal blood loss, and the ability to track over a wire guide to a precise location within a narrow vessel.

SUMMARY OF THE INVENTION

The foregoing problems are also solved and a technical advance is achieved in an introducer apparatus that includes co-extending splittable introducer sheaths, each having a different configurations. The use of co-extending introducers, whether coaxially arranged or coupled in another manner, permits advantageous use of the different properties or configurations of each in accessing a particular target site that may otherwise be difficult to reach. Typically, the introducer apparatus includes a first outer introducer sheath having a first shape and stiffness, which is used to reach a first target site. The smaller, inner introducer sheath uses the first sheath as a pathway and utilizes its increased flexibility and/or a second shape to advantageously reach a second, more distal target site that would otherwise be difficult to access using the outer introducer.

In one embodiment of an introducer apparatus used to place a pacemaker or defibrillator lead through the coronary sinus to stimulate the left side of the heart, the introducer apparatus includes an outer splittable introducer sheath and at least a second splittable introducer sheath that is coaxially inserted therein. The inner introducer sheath, which is usually introduced following initial placement of the outer introducer sheath, is designed to extend beyond the distal end of the outer introducer sheath into the coronary sinus to reach a coronary vessel for placement of a left-side lead. Preferably, the introducer sheaths comprise molecularly oriented (non-isotropic) polytetrafluoroethylene (PTFE) such as that used in the PEEL-AWAY™ Introducer Sheath, although pre-scored or other types of splittable introducer sheaths may be used for certain clinical applications.

In the embodiment used to place left-side pacing or defibrillator leads, the distal tip of the first introducer sheath is designed to be placed at the ostium to, or just within the coronary sinus. To facilitate this, the first introducer sheath includes at least one preformed bend that approximates the vasculature through which the sheath is navigated, thereby reducing the likelihood of kinking the sheath during its introduction. The first introducer sheath is designed to be introduced into a larger vessel, usually over a wire guide in combination with a steerage member, such as an internal dilator, and advanced to a first target site, such as the coronary sinus. The first dilator is then removed from the outer introducer sheath and the second introducer sheath is advanced over the wire guide through the outer sheath and maneuvered to a second, more distal target site where the lead or other device is to be placed. A second dilator or obturator can be used in combination with the inner introducer sheath as it is advanced into the smaller vessel. The second introducer is partially constrained and protected by the larger first introducer sheath during its initial path to the first target site. At that point, it is advanced from the distal tip of the outer introducer sheath until it reaches the second target site. Optionally, the inner introducer sheath itself may be shaped to generally correspond to that of the outer introducer sheath and provide greater protection against kinking, or it can be designed to assume the shape of the outer introducer sheath when placed therein. Additionally, a curve may be added to the distal portion of the inner introducer sheath to facilitate access of the desired site, which often involves making a relatively acute lateral bend, such as the case with the coronary sinus ostium and ostium cardiac veins.

In another aspect of the invention, a preformed obturator may be used with either or both introducer sheaths to help steer, position or rotate the mated sheath through the vasculature. For example, in an application used to place pacing or defibrillator leads into the coronary sinus and coronary veins, an obturator can be placed into the inner sheath as it tracks over the wire guide to help provide the torque and steerability needed to make the tight turn from the coronary sinus into a coronary vein. To allow for maximum maneuverability, the obturator is given a shape that is compatible with the shape of the introducer sheath to allow for maximum maneuverability. The obturator includes a small central lumen so that both it and the introducer sheath can be fed over a wire guide already in place at the target site. After the introducer sheath and obturator are advanced to the target site, the obturator is removed. Another method of positioning the introducer apparatus includes use of a steerable or deflecting tip catheter or wire guide within the passageway of the sheath. The steerable device is usually removed from the outer introducer sheath for placement of the inner introducer sheath through which the lead or other device is navigated to the ultimate target site. As an alternative to adding one or more preformed curves to the introducer sheaths themselves and/or the steerage members used in their placement, the steerable device may be used as the sole means for providing a curved shape to outer and/or inner introducer sheaths.

Still another aspect of the invention includes adding radiopaque markings to the distal end of inner and/or outer introducer sheaths, dilators, or obturators to augment visualization under fluoroscopy. Radiopacity can achieved by incorporating radiopaque powders, such as barium sulfate or tantalum powder, into the polymer comprising the sheath material, or a separate radiopaque marker, e.g., a metal band, or an annular ring of radiopaque paint or other type of indicia can be affixed to, or printed onto the introducer sheath.

Yet still another embodiment of the invention includes adding an inflatable balloon to the distal portion of the inner or outer introducer sheath which provides a seal against backflow during injection of contrast media. During certain placement of the devices within the coronary vasculature or other vessels, it is often desirable to be able to inject contrast media to improve visualization under fluoroscopy. In some situations, especially in the cardiac veins, the backflow of blood prevents the injected media from traveling to the desired site. The balloon is made to be carried away either intact, by being attached to only one half of the splittable shaft or by comprising two separate balloons that are attached to the respective halves of the splittable sheath, or the balloon is designed to split into two or more portions by including a predetermined separation line, such as a seam, that splits the balloon open when the shaft is split.

In still yet another embodiment, either the first or second introducer sheath can include a retention means to help prevent dislodgement from the target site. This can include one or more inflatable balloons or other atraumatic elements, such a series of bidirectional projections that prevent egress of the device.

DETAILED DESCRIPTION

Figures 1, 2:
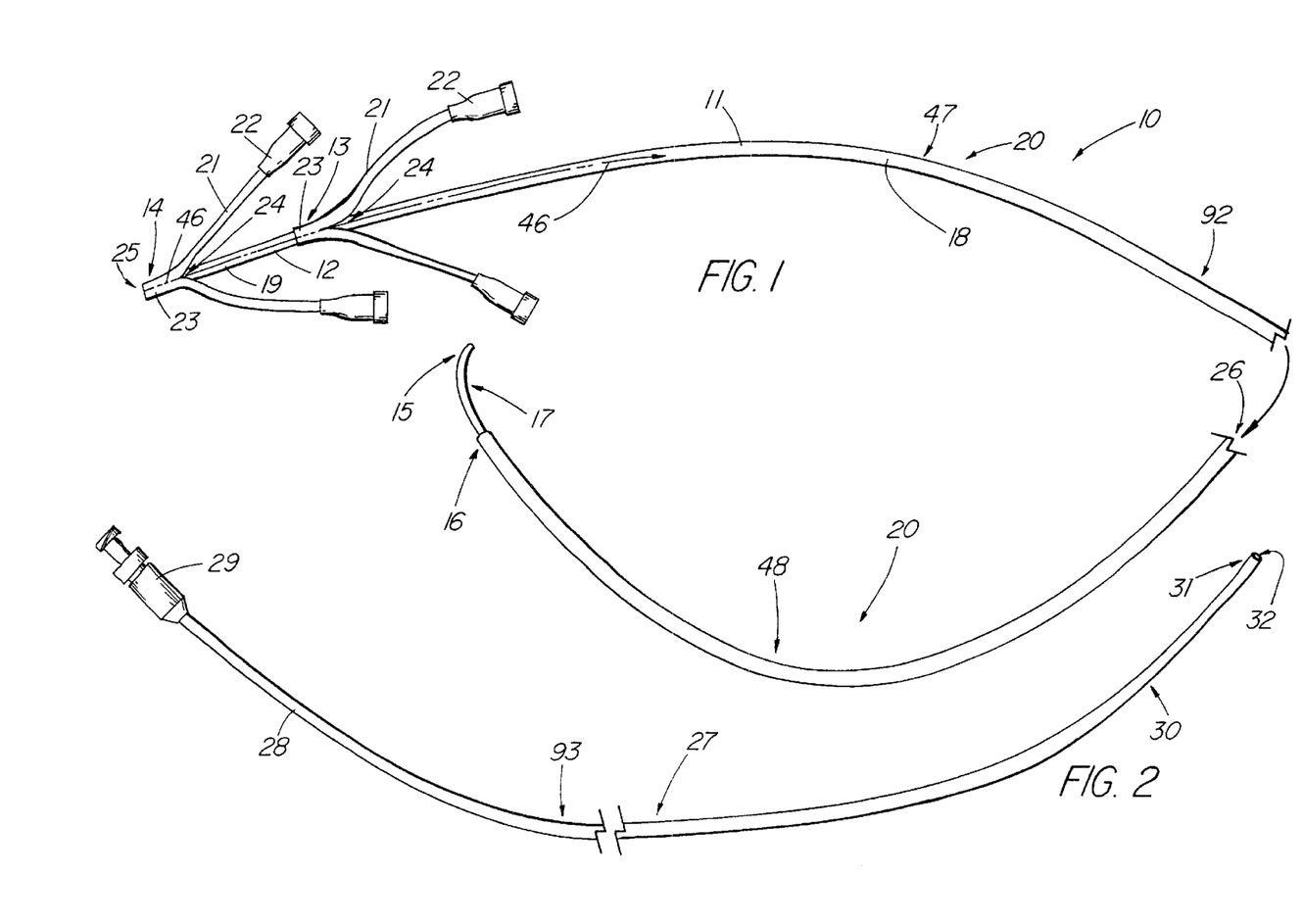
FIG. 1 depicts a side view of an embodiment of the present invention.
FIG. 2 depicts an obturator used with the embodiment of FIG. 1.

FIG. 1 depicts the illustrative embodiment of an introducer apparatus 10 of the present invention which comprises a first introducer sheath 11, such as an outer introducer sheath 11, and a second introducer sheath 12, such as a coaxial inner introducer sheath 12. The first and second introducer sheaths 11,12 are designed to be splittable longitudinally so that the separated sheath portions can be removed from within the body of a patient while the device introduced therethrough, such as a pacemaker or defibrillator lead, can remain in place without being dislodged during their removal. The first and second introducer sheaths 11,12 are designed to co-extend into the bodily passage at some point during the procedure. As used herein, co-extending means that the two introducer sheaths can be introduced simultaneously or one sheath can introduced prior to the other, e.g., the outer introducer being initially placed to facilitate subsequent placement of the second introducer. In most applications, it is preferred that the first and second introducer sheaths 11,12 co-extend coaxially with the smaller (and usually less stiff) introducer being introduced inside a passageway of the first introducer. The passageway can be internal, such as the main passageway 26; however, it may be external, such as a series of loops or other guides attached to the first introducer sheath 11 that allow the second introducer sheath 12 to be introduced alongside the first introducer sheath in a non-coaxial arrangement. Additionally, the first and second introducer sheaths can be so configured to include a longitudinal coupling mechanism, such a track system whereby one introducer has a channel or receiving means to receive a corresponding feature on the other introducer, thereby allowing the two sheaths to be slidably coupled together at some point during a procedure. In another embodiment, the first and second introducer sheaths can be fixedly interconnected. For example, the inner introducer sheath 12 can be designed to evert from the outer introducer sheath 11 whereby it is connected about its proximal end 14 to the distal end 16 of the outer sheath 11 by a sleeve of a flexible fabric or polymer material such as expanded polytetrafluoroethylene (ePTFE).

In the illustrative embodiment of FIG. 1, the first introducer sheath 11 serves as an outer sheath for receiving the second introducer sheath 12, which is appropriately sized for introduction through the outer sheath passageway 26. In the illustrative embodiment, the outer introducer sheath 11 is sized to be initially introduced through the lumen of a vessel or duct to a first target site. In the embodiment of FIG. 1, which is particularly configured for navigating the subclavian vein and into the heart to place a pacemaker or defibrillator lead into the coronary sinus vein to reach and stimulate the left side of the heart, the preferred sheath diameter would range from 8 to 12 Fr, with a most preferred diameter of about 10 Fr. After the outer introducer sheath 11 has been placed at or within the first target site, the smaller introducer sheath 12 is advanced through the outer introducer sheath 11 to access a second target site which usually comprises a duct or vessel with a smaller diameter than the first target site and which could not be safely accessed by the larger outer introducer sheath 11. In this embodiment, the inner introducer sheath 12 normally ranges in diameter from about 5 to 8 Fr, with a most preferred diameter of about 7 Fr (when used with a 10 Fr outer introducer sheath 11).

Introducer sheath 11, 12 embodiments of the present invention, such as FIGS. 1–3a, that are designed for accessing remote sites within the body that usually comprise smaller, distally located vessels, must be made significantly longer than standard 12–15 cm introducer sheaths such as those used in the placement of standard pacing or defibrillator leads. Depending on the application, the introducer sheaths 11,12 may range in length from 20 to 90 cm, with most applications utilizing sheaths in the 25–65 cm range, the upper limit being more of a practical one due to the desire to limit the portion extending from the patient. For example, in the illustrative embodiment of FIG. 1, configured for placement of a cardiac device, such as a biventricular pacemaker lead or defibrillator lead, into the coronary sinus of an adult patient, the outer introducer sheath 11 measures approximately 45–55 cm in length and the inner introducer sheath 12 is approximately 55–65 cm in length, with the most preferred lengths for adult patients being approximately 50 and 60 cm, respectively. Younger patients or small adults might require sheaths sized anywhere from 30 to 60% smaller than these ranges, e.g., outer and inner sheaths 11,12 being 35–45 and 45–55 cm, respectively.

Because the longer introducer apparatus is usually required to be navigated along a more tortuous path than a standard splittable introducer, it is desirable, but not essential, to add at least one preformed bend 20 to the outer introducer sheath 11 that at least somewhat corresponds in shape to the intended anatomical pathway. This helps in the navigation of the sheath to the target site and reduces the likelihood of the sheath becoming kinked while negotiating a bend. It is not necessary that the preformed bends or bends exactly match the radii and shapes of the bends of the particular target vessels; however, the bend(s) should be formed in such a manner that it significantly reduces the bending stress on the sheath when negotiating the bend of the vessel or duct and/or orients the distal end 16 of the introducer into a favorable position to access the desired target site. For example, the embodiment of FIG. 1, used to access the coronary sinus, has both a proximal bend 47 having a radius falling within the range of 2.5 to 3.5" and a distal bend 48 having a radius generally falling with the range of 1.5 to 2.75". Together, the proximal and distal bends 47,48 generally form a serpentine configuration 92. The distal bend 48 facilitates navigation through the curvature of the subclavian 34 and innominate veins 35, shown in FIG. 3. As the first (outer) sheath 11 is maneuvered through the superior vena cava 36 into the right atrium 37, it is rotated such that the distal curve 48 is oriented toward the target site, the ostium 38 of the coronary sinus, while the portion of the sheath having the proximal curve 47 can permit easier navigation of the introducer sheath through the subclavian-innominate vein bend. Typically, the distal bend has a tighter radius in order to provide posterolateral access to the coronary sinus ostium. When a different embodiment of the present invention is used, for example to access the renal vasculature, urinary system, bronchial tree, cranial arteries, etc., the preformed curve(s) 20 would be configured to address the particular anatomical requirements. The inner introducer sheath 12 can either have a generally straight shaft 19 or include preformed bends that approximate those found in the outer introducer sheath 11. As the smaller diameter and therefore, more flexible inner introducer sheath 12 is advanced through the outer introducer sheath 11, it tends to assume the shape of the outer introducer, especially if it also has been configured to include its own preformed bends that are located correspondingly. For certain embodiments, such as that of FIG. 1, it may be advantageous for the inner introducer sheath 12 to include a distal curved portion 17 to facilitate access of a particular vessel or duct. It should be noted that although the present invention is particularly useful for reaching a remote location within the body, thus requiring introducers of usually long length, a co-extending splittable introducer sheath of a more conventional length (i.e., less than 20 cm) should be considered within the scope of the invention as well.

Figure 12:
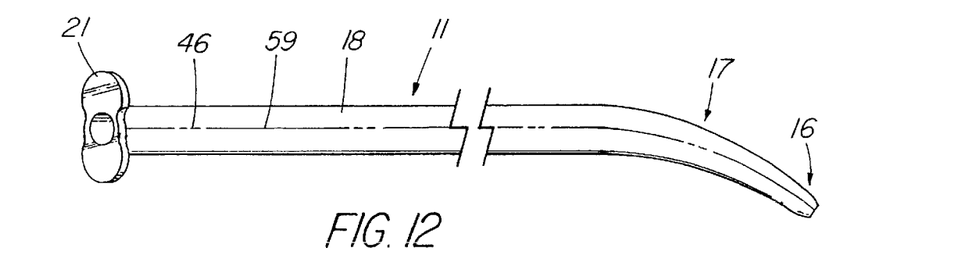
FIG. 12 depicts a pictorial view of a fifth embodiment of the present invention.

The inner and outer introducer sheaths 11,12 are made splittable by use of any well-known means or material that permits each sheath to be separated longitudinally along a relatively predictable path, such as a predetermined split line 46 by manual force generally applied at the proximal end 13,14 of the shaft 18,19. The sheath 11,12 is usually, but not necessarily separated into two or more portions, thereby opening a fissure along the length of the shaft 18,19 that permits its removal from around the lead or other indwelling device situated therein, such that the indwelling device can remain within the patient as the introducer sheath is removed. The predetermined split line 46 is a pathway along the length of the sheath through which the tear or split progresses due to properties of, and/or features incorporated into the sheath material. It is naturally preferred that the means to split the sheath be able to withstand being subjected to a curve to the degree required by the particular application without kinking or premature separation. In the illustrative embodiment a splittable polymer is used such as molecularly oriented, non-isotropic PTFE that is used to make the PEEL-AWAY® Introducer Sheath (Cook Incorporated, Bloomington, Ind.) which is fully described in U.S. Pat. Nos. 4,306,562 to Osborne and U.S. Pat. No. 4,581,025 to Timmermans. In an alternative embodiment, sometimes known in the art as a 'crack' and 'peel' introducer, the sheath can be made splittable by adding at least one preweakened feature 59, such as a score line extending longitudinally along the sheath as depicted in FIG. 12. The longitudinal preweakened feature 59 could include anywhere from one or more orthogonal predetermined split lines 46, as shown, to a helical type arrangement that may comprise only a single predetermined split line 46.

Figures 3, 3A:
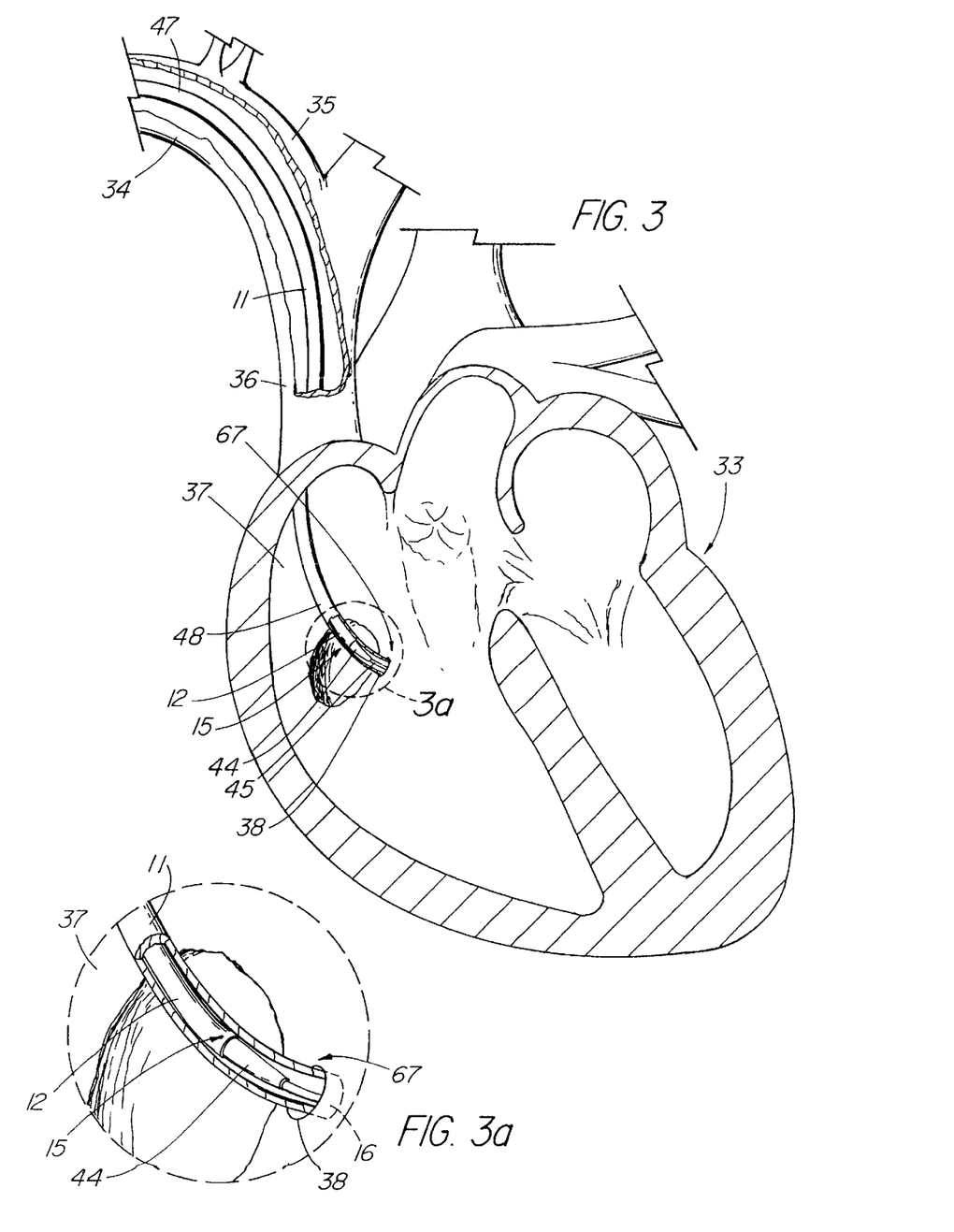
FIGS. 3–3a depict the device of FIG. 1 being used in the coronary sinus.
Figure 4:
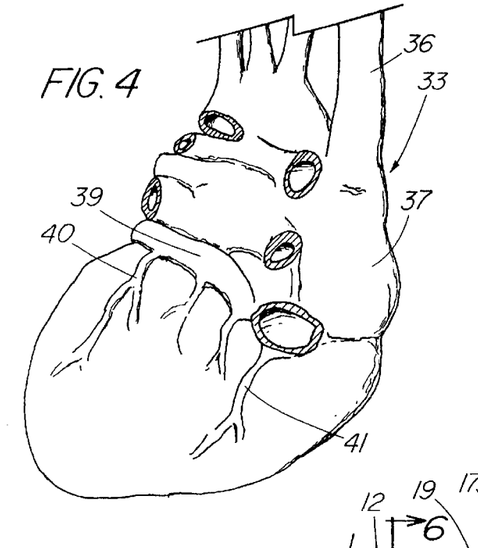
FIGS. 4–4a depict use of the device of FIG. 1 in the coronary sinus with an obturator.
Figure 4A:
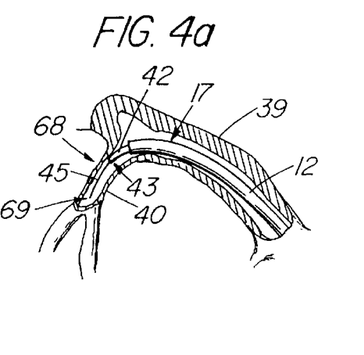

As depicted in FIGS. 3–3a and 4a, the introducer apparatus 10 is normally introduced over a wire guide. In the illustrative embodiment, a small diameter wire guide 45 with good torqueability in combination with an atraumatic tip is preferred, such as the COOK ROADRUNNER™ FIRM™ Wire Guide or COOK TORQ-FLEX® Wire Guide (Cook Incorporated, Bloomington, Ind.). Generally, the tip 69 of the wire guide 45, which may be angled, is guided to at least the first target site 67 (i.e., about where the distal tip 16 of the outer introducer sheath 11 is to be placed), and possibly to the second target site 68 to which the distal tip 15 of the inner introducer sheath 12 is to be placed. In the illustrative example, the wire guide 45 is first placed into the ostium 38 leading to the coronary sinus 39 which represents the first target site 67. Then, as in the case of biventricular pacing, the wire guide 45 is subsequently guided through the coronary sinus 39 and down a cardiac vein branching from the coronary sinus 39 (the second target site 68), for example, the posterior vein of the left ventricle 40 as shown in FIG. 4a, or another vein such as the middle cardiac vein 41 shown in FIG. 4.

While not always necessary, it is often advantageous to include a steerage member, such as a dilator, obturator, deflectable tip device, etc., for assisting with the introduction and placement of the introducer sheaths 11,12. As used herein, a 'steerage member' is defined as a device or apparatus that is used in conjunction with an introducer sheath 11,12 during advancement through a bodily passage to assist in some manner with the placement of the sheath at a target site. Normally, a steerage member is a placed inside the passageway 25,26 of the sheath to provide the desired torqueability, maneuverability, or shape for improved navigation or reduced risk of kinkage. In the case of a dilator, the tapered tip can be useful when guiding the sheath into a narrowed lumen or opening. In the illustrative embodiment of FIGS. 1–2, a dilator can be advantageously used with the outer introducer sheath 11 for reaching the coronary sinus. With the wire guide 45 in place, a first dilator 27, comprising a shaft 28 and proximal hub 29 and depicted in FIG. 2, can be used inside the outer introducer sheath 11 of FIG. 1 to facilitate its introduction to the target site, which in this embodiment, requires maneuvering through the right atrium 37 and into the ostium 38 of the coronary sinus 39. The shaft 28 of the first dilator 27, which can be made of PTFE or an other suitable polymer, includes a distal taper 30 and narrow tip 31, with a passageway 32 sufficiently large to accommodate an appropriate wire guide 45. The purpose of the first dilator 27 is to provide a relatively atraumatic means to guide the tip of the first introducer sheath 11 through the vasculature and to access a relatively small opening such as the coronary sinus ostium 38. Without the dilator 27, increased precision would be required to advance the distal tip 16 of the outer introducer sheath 11 into the ostium 38 opening. As with the mated introducer sheaths 11,12, the dilator 27 may be given a preformed shape 93 that corresponds to that of the other devices with which it is used. Alternately, the preformed shape 93 of the dilator can provide a curved configuration to otherwise straight introducer sheaths 11,12, especially if having one or more preformed curves is primarily important during introduction and is not particularly advantageous once the sheath has been placed within the patient. It should be noted that upon insertion therewithin, it is possible for the preformed inner member, such as a dilator 27, obturator, or inner introducer sheath 12, to either elastically or plastically deform the outer member, such an introducer sheath 11,12, depending on the physical properties of the inner and outer members.

Once the outer introducer sheath 11 is in place, the dilator 27 is removed and the inner introducer sheath 12 is inserted therethrough. As with the outer introducer sheath 11, a second dilator 44, shown in FIGS. 3–3a, can be used to guide the inner introducer sheath further into the coronary sinus 39 to a more distal target site 68, such as the posterior vein of the left ventricle 40 as depicted in FIG. 4a. Once the inner introducer sheath 12 is advanced to the second target site 68 within the vasculature, the second dilator 44 is removed and the pacing lead or other device is advanced through the inner introducer sheaths 12 to the second target site 68 or a more distal location. Once the lead or device has been properly placed, the outer introducer sheath 11 (of FIG. 1) is then removed by splitting it into two portions from around the indwelling lead. This is accomplished by grasping the handles 22 attached to the ears 21 extending from the sheath material. The shaft 18 is torn into two separate portions along the predetermined split line 46 starting from the cut point 24 in the material. As fabricated, the material forms a folded cuff 23 at the proximal end 13 of the outer introducer sheath 11 such that the material is initially torn in the proximal direction, then starting at the proximal end 13, is split along the predetermined split line 46 toward the distal 16 until the shaft 18 is completely split apart. Ultimately, the inner introducer sheath 12 will be removed in a manner similar to that of the outer introducer sheath with the shaft 19 also being torn along the predetermined split line 46 from the proximal end 14 to the distal end 15 until the shaft 19 separates and is removed from the patient.

Figure 13:
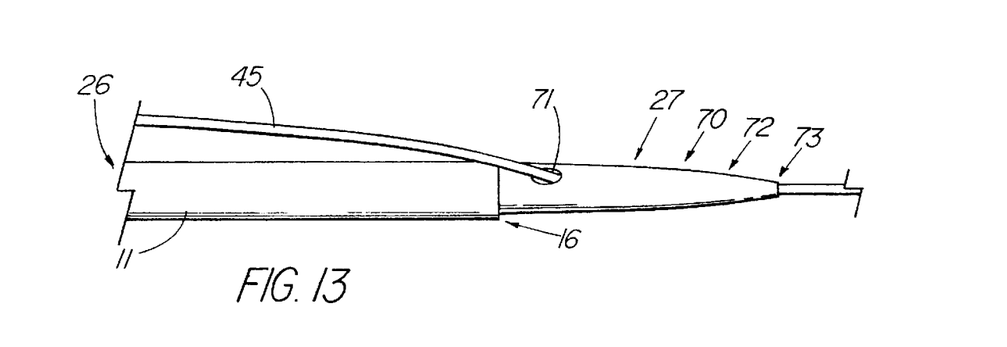
FIG. 13 depicts a side view of a second dilator embodiment of the present invention.

FIG. 13 depicts another method of using the introducer apparatus with a wire guide. In this embodiment, the first dilator 27 comprises a monorail dilator configuration 70 that includes a side opening 71 such that the wire guide 45 can feed into the central passageway 72 of dilator 70, rather than the introducer sheath 11 itself tracking over the wire guide 45 or the dilator and introducer sheath both tracking over the wire guide extending through the passageway 32 of the dilator shaft 28 of dilator 27. The monorail dilator can be used with either of the inner or outer introducer sheaths 11,12, such as those depicted in FIG. 1.

Figure 14:
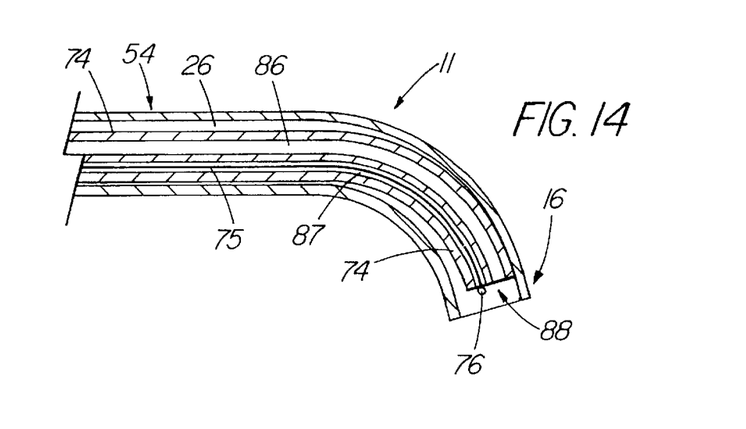
FIG. 14 depicts a partially sectioned view of the present invention being used with a steerable/deflectable positioning device.

To add stiffness to the inner introducer sheath 12 for increasing torqueability and pushability (as defined by common engineering testing standards), an obturator 42 may be used as shown in FIG. 4a. As with the introducer sheaths 11,12 and dilators 27,44, the obturator can include a passageway to allow for tracking over a wire guide. Preferably, the obturator is 42 designed to have the maximum amount of material and wall thickness with the smallest possible wire guide lumen to yield the maximum stiffness for providing good maneuverability. The obturator, which can be made of PTFE or another suitable polymer for fabricating sheaths, can include at least one preformed curve to facilitate steering, positioning, and rotation of the inner introducer sheath 12. Additionally, an obturator 42 can be used to assist with the positioning of the outer introducer sheath. Another method of positioning the introducer sheaths 11,12 into the target site, shown in FIG. 14, includes use of a well-known steerable or deflecting tip device 74, such as a catheter (e.g., an Electrophysiology (EP) Catheter) or a wire guide, in place of or in combination with a dilator or pre-formed obturator. By introducing or incorporating the steerable/deflectable device into an outer or inner introducer sheath 11,12 permits the tip of the sheath to be deflected into the optimum position for advancing the sheath to the target area or providing an improved position such that the inner introducer sheath 12 can be then advanced to the target site. The steerable/deflectable device 74 may include a passageway 86 for a wire guide, and be integral with either of the sheaths 11,12 or represent a separate component of the introducer apparatus 10. A separate steerable/deflectable steerage device 74 can being used to reach the vicinity of the ostium or target vessel such that the introducer sheath or sheaths 11,12 can then be advanced thereover to the desired target site. In the illustrative embodiment, the steerable/deflectable device 74 further includes a second passageway 87 that houses a deflection control means 75, such as a flexible rod, wire, suture, etc., that is attached about the distal end 88 of the steerable/deflectable device 74 and extends proximally to a control handle (not shown) that affects the degree of deflection of the introducer sheath tip 16. The illustrative embodiment of FIG. 14 represents one example of how to make a steerable/deflectable device 74 among many alternative methods that are known in the medical arts. The choice of the deflection control means 75, how or whether it is attached, and the specific configuration of the steerable/deflectable device 74, depends largely on intended use and physician preference. Again, it should be noted that the steerable/deflectable device 74 can be used with an introducer sheath 11,12 having one or more pre-formed bends 20, or it can be used to provide a curved configuration to an otherwise straight introducer sheath 11,12 when the steerable/deflectable device 74 is deployed therewithin.

Figure 5:
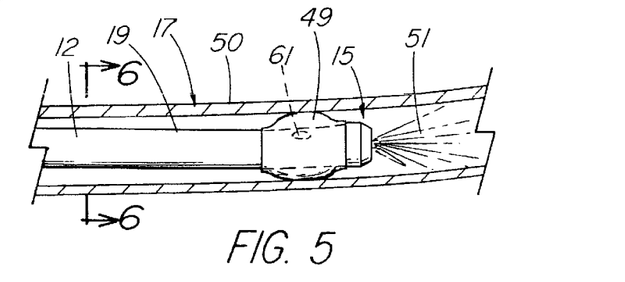
FIG. 5 depicted a side view of a second embodiment of the present invention that includes a balloon used inside a vessel.
Figure 6:
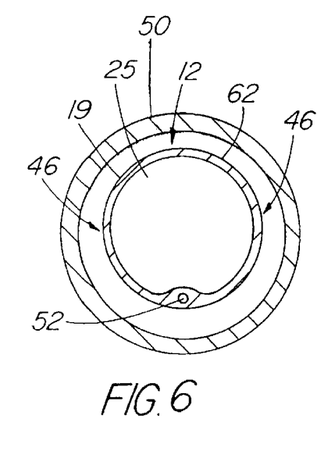
FIG. 6 depicts a cross-sectional view taken along line 6—6 of FIG. 5.
Figure 15:
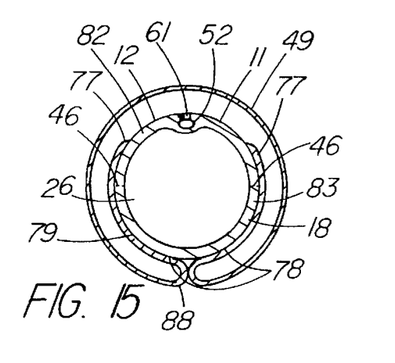
FIGS. 15–16 depict cross-sectional views of separate balloon embodiments used with the present invention.
Figure 16:
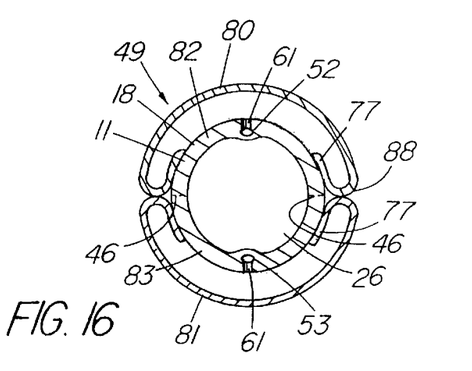

FIG. 5 depicts an embodiment of inner introducer sheath 11 that includes an expandable member 49, such as an inflatable balloon 49 or other well-known occlusion mechanism, mounted to the distal portion 17 of the shaft 19. The balloon 49 communicates with a well-known inflation means, such as a syringe, via an inflation port 61 and a separate inflation lumen 52, as depicted in FIG. 6. The inflatable balloon 49 can be made from a number of well-known compliant materials, such as latex or silicone, or a well-known noncompliant material, such as polyethylene teraphthalate (PET) or a polyamide fabric, depending on the medical application. In the illustrative embodiment, the balloon 49 is made of PET. By sizing the balloon 49 to the target vessel, it helps prevent against overinflation that could lead to rupture of the vessel 50. The balloon 49 of this embodiment is used to temporarily occlude the vessel 50 while contrast media 51 is injected into the vein to improve fluoroscopic guidance of the device to the target site. Without occlusion of the vessel 50 to prevent retrograde flow, the contrast media 51 may be carried back with the blood flow and thus not travel downstream to a sufficient degree to permit adequate imaging of the portion of the vessel containing the target site. The balloon 49 can be mounted on either the outer or inner introducer sheath 11,12, depending on how the particular embodiment is used in the body. To allow the balloon 49 to be carried away with the splittable introducer sheath portions 82,83, the balloon 49 can configured such that the primary attachment points 77 are on a first half 82 of the introducer shaft 18, as depicted in FIG. 15, with the balloon extending circumferentially around the shaft from the respective attachment points 77. The lateral edges 88 of the balloon 49 wrap around the shaft 18 and meet over the second half 83 where they can be affixed thereto using a bonding means 78 that will readily yield to shearing forces that result from the shaft being split into the two portions 82,83. Because the balloon 49 is affixed to the second half 83 by a weaker bonding means 78 than that joining the balloon 49 to the first half 82, the entire balloon 49 is carried away intact with the first halve 82 during separation of the shaft 18. As shown in FIG. 16, another method that allows the balloon to separate is to have two adjacent balloons 80,81, each attached to opposite halves 82,83 of the shaft 18, separated by the predetermined split lines 46, and together, inflate to function as a single composite balloon 49 capable of occluding the vessel. The first balloon 80 is attached to the first half 82 of the introducer shaft 18 where is communicates with a first inflation lumen 52. The first balloon 80 is configured into a hemispherical shape that generally wraps around and covers the surface of the first half 82. The second balloon 81 is attached to the second half 83 of the shaft 18 where it communicates with a second inflation lumen 53. It generally covers the surface of the second half 83 and abuts the first balloon 80 along the predetermined split lines 46. In a variation of this embodiment, the first balloon 80 can be larger than the second balloon 81 with its lateral edges 88, but not the attachment points 77, extending over the predetermined split lines 46 to abut with the smaller second balloon 81. It may not be necessary for the balloon portion 81,82 to completely surround the circumference of the shaft 18 to accomplish the goal of infusing contrast agent that remains for a sufficient period to allow diagnostic imaging.

Figure 17:
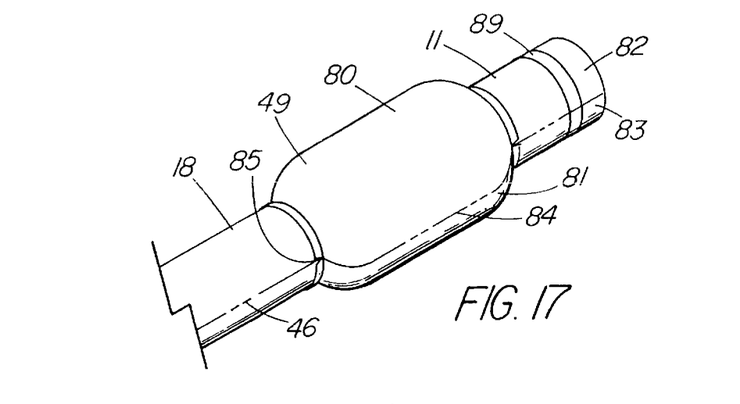
FIG. 17 depicts a pictorial view of a splittable balloon used with the present invention.

Yet another method of allowing an introducer sheath 11,12 with a balloon 49 to split, is shown in FIG. 17, wherein the balloon 49 includes a longitudinal weakened area 84 on the balloon 49 itself that allows the balloon to split into two portions as the shaft 18, to which it is attached, is separated. In the illustrative embodiment, the longitudinal weakened area 84 comprises a seam of overlapping balloon material, although the edges of the seam could be designed to abut each other. The edges of the seam 84 can be sealed, e.g., with heat, or secured together with a separate strip of material, such as a plastic tape, or an adhesive such as silicone such that the seam 84 can be readily pulled apart when force is applied to the degree required to split the shaft 18. To help facilitate the split, a cut point 85 can be positioned at the posterior edge of the material along the preweakened area 84 to provide a start to the intended split. The longitudinal weakened area 84 can also comprise a longitudinally extending zone in which the material has been mechanically weakened (e.g., via abrasion) or molecularly altered, e.g., a chemical or radiation treatment, such that the balloon will generally rupture along the preweakened area 84 when lateral force associated with the splitting of the shaft 18 is applied. Alternatively, a balloon material may be selected, such as a thin-wall latex or silicone, that permits rupture and separation of the balloon 49 when the shaft 18 is split apart, without requiring the addition of a longitudinal weakened area 84.

In addition to improving imaging by using the introducer apparatus 10 to inject contrast media, the apparatus itself can be made radiopaque by one of several well-known methods that include incorporation of radiopaque materials, such as barium sulfate, tantalum powder, etc. into the sheath polymer, the addition of markers, such as radiopaque metal bands, applying radiopaque indicia to the surface, etc. Both the outer and inner introducer sheaths 11,12 can be made radiopaque by at least one of these methods.

Figure 7:
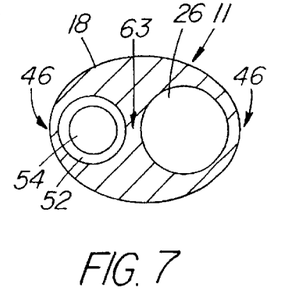
FIGS. 7–8 depict cross-sectional views of third and fourth embodiments of the present invention having a plurality of lumens.
Figure 8:
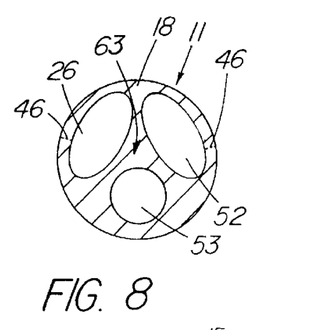

FIGS. 6–8 depict various embodiments of multiple lumen introducer sheaths. The embodiment of FIG. 6 depicts an inner introducer sheath 12 that includes a first, primary passageway 25 and a second passageway 52 incorporated into the sheath wall 62 that can be used as an inflation lumen or if made larger, could accommodate an ancillary device 54 such as a wire guide. FIG. 7 depicts a dual lumen outer introducer sheath 11 that includes a first passageway 26 and a smaller second passageway 52. The introducer apparatus 10 of this embodiment can be used coaxially with an inner introducer sheath (not shown) in the first passageway, or the outer introducer sheath 11 can be used alone with the lead or other device being placed through the first passageway. Typically, the second passageway is used for an ancillary device 54 as shown, which could include a wire guide or a well-known control means to help make the sheath steerable or deflectable. This could also include use of a steerable electrophysiology catheter or a control mechanism that operates in a similar manner, wherein the distal portion of the sheath can be manipulated via a well-known type of handle used for tip deflection that is connected to the proximal end of the sheath. The predetermined split lines 46 can be positioned about the shaft 18 such that they permit both passageways 26,52 to be peeled open and the sheath portions removed to allow a lead, wire guide, or other device to remain in place. The intraluminal wall 63 separating the first and second passageways can be made sufficiently thin to rupture when the shaft is being separated, or it can be given a weakened feature 64 that is added to the intraluminal wall during or after the extrusion process to facilitate rupture. If the outer introducer sheath 11 is only to be removed from over a single device, it may not be necessary to have the predetermined split line 46 intersect the second passageway 52 which can remain intact while still allowing the first introducer sheath 11 to be split and removed from the patient.

FIG. 8 depicts a three-lumen outer introducer sheath 11 that includes first and second passageways 26,52 that are split open longitudinally when the sheath separates. The third passageway 53, typically used for injection of contrast media or for an ancillary device, such as a wire guide, can be left intact as it is not necessary to expose the third passageway 53 if any device contained therein is removed prior to the separation of the shaft 18. Alternatively, the shaft 18 can be made to split along three predetermined split lines 46 if all three passageways 26,52,53 must be opened and exposed to remove devices that are left in place, or the intraluminal wall can be so designed to accomplish the same result with only two predetermined split lines 46.

Figure 9:
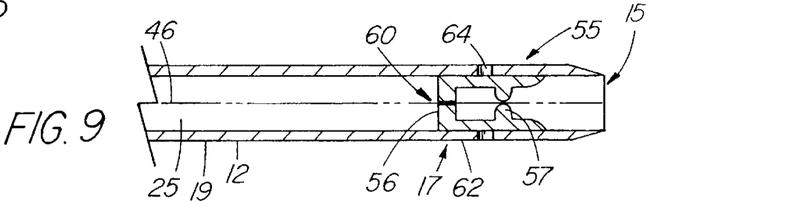
FIG. 9 depicts a sectioned side view of the present invention that includes an internal hemostatic valve.
Figure 10:
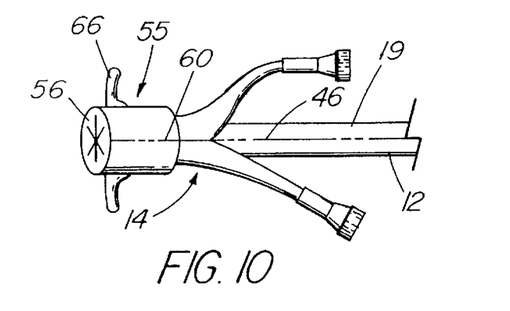
FIG. 10 depicts a side view of the present invention that includes an external hemostatic valve.

FIGS. 9–10 depict embodiments of the present invention that include a valve 55, such as a splittable hemostatic valve, to prevent loss of blood during an intravascular procedure, especially procedures of long duration such as coronary sinus or cardiac defibrillator lead placement. In the embodiment of FIG. 9, the hemostatic valve 55, preferably made of silicone, is insert molded into the passageway 25 of an inner introducer sheath 12 near the distal portion 17 of the shaft 19 with the silicone material flowing into apertures 64 made in the shaft wall 62 to help secure the hemostatic valve 55 and prevent longitudinal migration and allow the valve to be pulled apart with the shaft 19. To separate the hemostatic valve 55 when the sheath is separated, the valve body is given at least one line of fissure 60 extending therealong that can include a scored line or a thinned region such that the hemostatic valve halves rupture along the line of fissure 60 when the shaft 19 halves to which they are attached, are being split apart. Besides being insert molded, the hemostatic valve 55 can be made as a separate component and affixed within the shaft 19 using a well-known method such as gluing. The hemostatic valve 55 can vary in its configuration and may comprise a simple O-ring. The illustrative hemostatic valve 55 includes two primary seals in the integral valve body: a membrane 56 and an O-ring 57.

Figure 11:
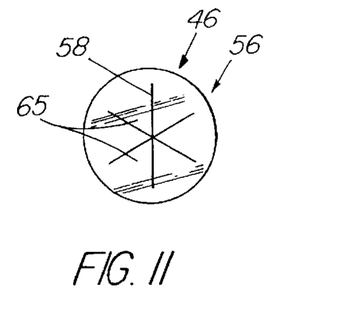
FIG. 11 depicts an end view of a membrane of the embodiment of FIG. 10.

The membrane depicted in FIG. 11 includes a series of slits 58 that define a number of valve leaflets 65 designed to help seal about an elongated device introduced therethrough. To facilitate separation of the hemostatic valve 55 along with the introducer sheath 11,12, it is usually desirable to affix or join the two together, preferably aligning the predetermined split line 46 of the introducer sheath 11,12 with the lines of fissure 60 of the hemostatic valve. This can be accomplished by gluing the hemostatic valve therein or allowing the silicone or polymer used to form the hemostatic valve to flow through apertures 64 (FIG. 9) made in the sheath wall 62 and cure to form a positive fixation that can withstand the forces required to separate the introducer apparatus 10 into two portions. FIG. 10 depicts an embodiment wherein a hemostatic valve 55 is included on the proximal end 14 of the inner introducer sheath 12.

The hemostatic valve 55 can be integrally attached to the introducer sheath 21 or made to be detachable as shown in FIG. 10 wherein the valve traverses the proximal end 13 of the outer introducer sheath 11. While an integral hemostatic valve 55 may be designed to split along with the introducer sheath shaft 19, in the detachable embodiment, the hemostatic valve is split apart separately prior to splitting the introducer sheath 11. This is accomplished by grasping the integral valve handles 66 and pulling them apart until the valve separates along the lines of fissure 60. The hemostatic valve 55 can be included on either the outer or inner introducer sheaths 11,12. To provide a seal between sheaths when used together, a hemostatic valve 55 consisting of an O-ring or similar structure can be either affixed within the passageway 26 of the outer introducer sheath 11 or to the exterior surface of the shaft 19 of the inner introducer sheath 12.

Figures 18, 19:
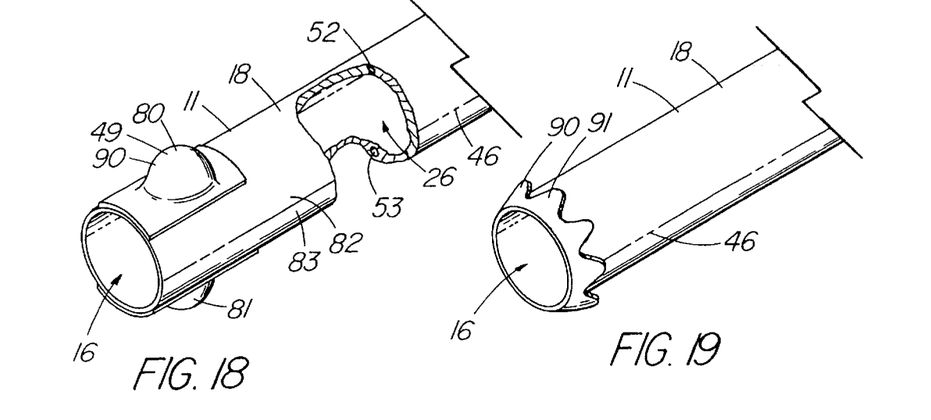
FIGS. 18–19 depict pictorial views of separate embodiments that include a retention means.

FIGS. 18–19 depict embodiments that include one or more retention members 90 located about the distal end 16 of the introducer sheath 11 that advantageously prevents or reduces unintended movement of the introduce sheath 11 during the procedure. This especially can be a problem when the friction caused by the withdrawal of the inner sheath or another indwelling device causes the introducer sheath 11 to dislodge from the intended target site. FIG. 18 depicts an introducer sheath 11 having a pair of expandable members 49 comprising a first balloon portion 80 affixed to a first half 82 of the shaft 18, and a second balloon portion 81 affixed to the second half 83 of the shaft 18, with the predetermined split lines extending therebetween. Unlike the occlusion balloon 49 depicted in 15–17, it is not necessarily desirable for the first and section balloon portions 81,82 to contact one another and surround the circumference of the shaft to provide a seal against fluid flow. Each balloon portion, which in this embodiment is a complete separate balloon 49, is inflated via dedicated second and third passageways 52,53 (inflation lumens) within the introducer sheath, with each communicating proximally with a common or separate inflation means, such as a syringe. Alternatively, a single expandable member may be sufficient, in certain applications, to prevent or inhibit migration of the introducer sheath. Additionally, more than two balloons 49 can be positioned about the shaft, including a longitudinal alignment at various points along the axis of the shaft, rather than the depicted circumferential arrangement. The expandable member 49 can simultaneously function as both a retention member 90 and an occlusion balloon 49 for injection of contrast media as depicted in FIGS. 5, 15–17.

FIG. 19 shows a second main embodiment of an introducer sheath 11 having a plurality of retention members 90 that comprise a plurality of bidirectional retention elements 91 located about the distal end 16 of the sheath. These bidirectional retention elements 91 can include a variety of configurations, but are preferably constructed of a material that is not traumatic to the tissues of the bodily passage. In the illustrative embodiment, the bidirectional elements comprise a series of annual projections that allow the introducer sheath 11 to be easily advanced, but provide limited resistance when the sheath 11 is urged in the opposite direction. The desired degree of the resistance to egress can be modified according to the anatomical and clinical requirements. Certainly, the bidirectional elements can be modified in size, number, and placement along the shaft 18 of the introducer sheath 11. For example, numerous, much smaller projections can be added to the outer surface of the sheath, or even formed in the outer surface of the shaft 18 material, to increase the coefficient of friction in one direction without significantly adding to the outer diameter of the sheath. While the outer introducer sheath 11 is often more prone to dislodgement during a procedure, it also may be desirable that the inner introducer sheath 12 can be modified to include one or more retention members 90 to reduce the possibility of its migration.

It should be understood that the present invention is not limited to a pair of introducer sheaths. It is within the scope of the invention to include one or more additional introducer sheaths inside one or more of the first and second introducer sheaths 11,12. For example, the outer introducer sheath 11 could be sized to accommodate two inner introducer sheaths 12 placed adjacent to one another to access two different target sites (e.g., left and right renal vein), or there could be three or more concentric introducer sheaths with the smallest introducer sheath accessing perhaps a third target site that either is more distal than the second target site, or requires a different curvature of the distal portion 17 than the second introducer 12 in order to be accessed.

It is thus seen that the present invention has utility in a variety of medical procedures, and variations and modifications of the introducer assembly of the present invention additional to the embodiments described herein are within the spirit of the invention and the scope of the claims.

What is claimed is:

1. A medical introducer apparatus, comprising:
   a first introducer sheath having a distal end, a proximal end and at least a first passageway extending therethrough;
   a second introducer sheath having a distal end, a distal portion, a proximal end, and at least a first passageway extending therethrough, the first and second introducer sheaths configured to be longitudinally splittable; the first and second introducer sheaths further configured to co-extend into a bodily passage, whereby the distal portion of the second introducer sheath is at least partly extendable beyond the distal end of the first introducer sheath;
   wherein the first introducer sheath includes a preformed bend in a portion of said sheath that extends in said bodily passage.

2. The introducer apparatus of claim 1 wherein the second introducer sheath is coaxially disposed within the first passageway of the first introducer sheath.

3. The introducer apparatus of claim 2 wherein the curvature of the at least one preformed bend has a radius of 10 cm or tighter.

4. The introducer apparatus of claim 2 wherein the first introducer sheath includes a plurality of preformed bends.

5. The introducer apparatus of claim 4 wherein the plurality of preformed bends include a distal bend and proximal bend, the distal and proximal bends formed such that the first introducer sheath generally comprises a serpentine configuration.

6. The introducer apparatus of claim 2 having an overall length of at least 20 cm.

7. The introducer apparatus of claim 6 wherein the first introducer sheath has a length of at least 35 cm, and the second introducer sheath has a length of at least 45 cm.

8. The introducer apparatus of claim 7 wherein the first introducer sheath has a length of at least 45 cm, and the second introducer sheath has a length of at least 55 cm.

9. The introducer apparatus of claim 2 wherein the distal portion of the second introducer sheath includes a preformed bend.

10. The introducer apparatus of claim 1 wherein at least one of the first introducer sheath and the second introducer sheath further includes an expandable member located about the distal end of the at least one of first and second introducer sheaths.

11. The introducer apparatus of claim 10 wherein the expandable member includes one or more inflatable balloons adapted to at least partially occlude a bodily passage.

12. The introducer apparatus of claim 1 wherein at least one of the first introducer sheath and the second introducer sheath further includes at least one retention element adapted for preventing retrograde migration of the at least one of first and second introducer sheaths.

13. The introducer apparatus of claim 1 further includes at least one steerage member adapted for placement within at least one passageway of at least one of the first introducer sheath and the second introducer sheath.

14. The introducer apparatus of claim 13 wherein at least one of the at least one steerage member selected from a group consisting of a dilator and an obturator.

15. The introducer apparatus of claim 13 wherein at least one of the at least one coaxial steerage member comprises a remotely controllable steerable member.

16. The introducer apparatus of claim 1 wherein at leas one of the first introducer sheath and the second introducer includes a plurality of passageways.

17. The introducer apparatus of claim 1 wherein at least one of the first introducer sheath and the second introducer includes a valve adapted to reduce retrograde flow of bodily fluids from within at least the first passageway thereof.

18. The introducer apparatus of claim 17 wherein said valve is longitudinally splittable.

19. The introducer apparatus of claim 1 wherein at least one of the first introducer sheath and the second introducer includes at least one of a radiopaque marker placed thereon or a radiopaque agent incorporated therewithin.

20. The introducer apparatus of claim 1, wherein each of said first and second introducer sheaths has a preformed bend.

21. A medical introducer apparatus, comprising:
   a first introducer sheath having a distal end, a proximal end and a first passageway extending therethrough;
   a second introducer sheath having a distal end, a distal portion, a proximal end, and a passageway extending therethrough, the second introducer sheath sized and configured for placement within the passageway of the first introducer sheath such that the distal portion of the second introducer sheath is at least partly extendable beyond the distal end of the first introducer sheath;

wherein the first and second introducer sheaths comprise a molecularly oriented, non-isotropic polymer material such that the first and second introducer sheaths can be longitudinally split along at least one predetermined split line and removed from the patient;

wherein at least one of the first introducer sheath and the second introducer sheath includes a preformed bend in a portion of said sheath that extends in said bodily passage.

22. The introducer apparatus of claim 21 wherein the polymer material comprises polytetrafluoroethylene.

23. The introducer apparatus of claim 21 wherein the first introducer sheath includes a plurality of preformed bends.

24. The introducer apparatus of claim 23 wherein the plurality of preformed bends includes a distal bend and proximal bend, the first introducer sheath being so configured that when the first introducer sheath is placed within the vascular system of a patient such that the distal end of the first introducer is generally located within the region including the right atrium and coronary sinus of the patient, the proximal bend being generally located within, and generally conforming to the curvature of the right subclavian and innominate veins of the patient, while the distal bend is at least partially located within the right atrium and configured such that the distal end of the first introducer sheath is oriented toward the ostium of the coronary sinus of the patient.

25. The introducer apparatus of claim 23 wherein the first introducer sheath has a length of at least 35 cm, and the second introducer sheath has a length of at least 45 cm.

26. The introducer apparatus of claim 25 wherein the first introducer sheath has a length of at least 45 cm, and the second introducer sheath has a length of at least 55 cm.

27. The introducer apparatus of claim 23 further includes at least one steerage member adapted for placement within the passageway of at least one of the first introducer sheath and the second introducer sheath.

28. The introducer sheath of claim 21, wherein at least one of the first introducer sheath and the second introducer sheath includes a longitudinally splittable valve adapted to reduce retrograde flow of bodily fluids from within at least the first passageway thereof.

29. A medical introducer apparatus, comprising:

a first introducer sheath having a distal end, a proximal end and one or more passageways extending therethrough;

a second introducer sheath having a distal end, a distal portion, a proximal end, and one or more passageways extending therethrough, the first and second introducer sheaths configured to be longitudinally splittable; the first and second introducer sheaths further configured to co-extend into a bodily passage, whereby the distal portion of the second introducer sheath is at least partly extendable beyond the distal end of the first introducer sheath;

at least one steerage member adapted for placement within at least one of the one or more passageways of at least one of the first introducer sheath and the second introducer sheath, the at least one steerage member being so configured such that placement thereof within a selected one of the one or more passageways permits the at least one of the first introducer sheath and the second introducer sheath to assume a configuration having at least one curve extending therealong during passage thereof through a bodily passage.

30. The introducer apparatus of claim 29 wherein at least one of the at least one steerage member includes one or more preformed bends.

31. The introducer apparatus of claim 29 wherein at least one of the at least one steerage member comprises a remotely controllable steerable member.

32. A medical introducer apparatus, comprising:

a first introducer sheath having a distal end, a proximal end and a first passageway extending therethrough, the first introducer measuring 45 to 55 cm in length and further having a proximal bend and a distal bend, the first introducer sheath being so configured that when the first introducer sheath is placed within the vascular system of a patient such that the distal end of the first introducer is located within the right atrium of the patient, the proximal bend is generally located within, and generally conforms along the curvature of the right subclavian and innominate veins of the patient, while the distal bend is at least partially located within the right atrium and configured such that the distal end of the first introducer sheath is oriented toward the ostium of the coronary sinus of the patient;

a second introducer sheath having a distal end, a distal portion comprising a preformed curve, a proximal end, and a first passageway extending therethrough, the second introducer sheaths measuring 55 to 65 cm in length and further sized and configured for placement within the first passageway of the first introducer sheath such that the distal portion of the second introducer sheath is at least partly extendable beyond the distal end of the first introducer sheath;

at least one steerage member adapted for placement within the first passage of at least one of the first introducer sheath and the second introducer sheath, the at least one steerage member so configured such that placement thereof within the first passage of at least one of the first introducer sheath and the second introducer sheath permits the at least one of the first and second introducer sheaths to assume a configuration having at least one curve extending therealong during passage thereof through a bodily passage;

wherein the first and second introducer sheaths comprise molecularly oriented, non-isotropic polytetrafluoroethylene such that the first and second introducer sheaths can be longitudinally split along at least one predetermined split line and removed from the patient.

33. The introducer sheath of claim 29, wherein at least one of the first introducer sheath and the second introducer sheath includes a longitudinally splittable valve adapted to reduce retrograde flow of bodily fluids from within at least the first passageway thereof.

* * * * *